US012076099B2

(12) United States Patent
Shrivastava et al.

(10) Patent No.: US 12,076,099 B2
(45) Date of Patent: Sep. 3, 2024

(54) PROJECTION OPERATOR FOR INVERSE KINEMATICS OF A SURGICAL ROBOT FOR LOW DEGREE OF FREEDOM TOOLS

(71) Applicant: Verb Surgical Inc., Santa Clara, CA (US)

(72) Inventors: Apoorv Shrivastava, Santa Clara, CA (US); Renbin Zhou, Santa Clara, CA (US); Haoran Yu, Santa Clara, CA (US); Seungkook Yun, Santa Clara, CA (US); Ellen Klingbeil, Santa Clara, CA (US)

(73) Assignee: Verb Surgical Inc., Santa Clara, CA (US)

( * ) Notice: Subject to any disclaimer, the term of this patent is extended or adjusted under 35 U.S.C. 154(b) by 516 days.

(21) Appl. No.: 17/368,221

(22) Filed: Jul. 6, 2021

(65) Prior Publication Data

US 2023/0009907 A1 Jan. 12, 2023

(51) Int. Cl.
*G06F 17/00* (2019.01)
*A61B 34/00* (2016.01)
*A61B 34/30* (2016.01)
*A61B 34/35* (2016.01)
*B25J 9/16* (2006.01)

(52) U.S. Cl.
CPC .............. *A61B 34/35* (2016.02); *A61B 34/25* (2016.02); *A61B 34/30* (2016.02); *B25J 9/1689* (2013.01)

(58) Field of Classification Search
CPC ......... A61B 34/35; A61B 34/25; A61B 34/30; A61B 2017/00203; A61B 2017/00216; B25J 9/1689; G05B 2219/39079; G05B 2219/45123

USPC ......................................................... 700/245
See application file for complete search history.

(56) References Cited

U.S. PATENT DOCUMENTS

| | | | | |
|---|---|---|---|---|
| 8,600,551 B2 * | 12/2013 | Itkowitz | ................. | A61B 34/77 700/250 |
| 8,666,544 B2 * | 3/2014 | Moll | ....................... | A61B 34/30 700/1 |
| 9,439,556 B2 * | 9/2016 | Pandya | ................. | A61B 1/3132 |
| 10,149,729 B2 * | 12/2018 | Smaby | .................... | A61B 34/70 |

(Continued)

FOREIGN PATENT DOCUMENTS

| | | |
|---|---|---|
| KR | 20150127129 A | 11/2015 |
| WO | 2022046053 A1 | 3/2022 |
| WO | WO-2022159229 A1 * | 7/2022 ............. A61B 34/74 |

OTHER PUBLICATIONS

Master-slave mapping and slave base placement optimization for intuitive and kinematically robust direct teleoperation (Year: 2012).*

(Continued)

*Primary Examiner* — Ronnie M Mancho
(74) *Attorney, Agent, or Firm* — Lempia Summerfield Katz LLC

(57) ABSTRACT

For teleoperation of a surgical robotic system, the control of the surgical robotic system accounts for a limited degree of freedom of a tool in a surgical robotic system. A projection from the greater DOF of the user input commands to the lesser DOF of the tool is included within or as part of the inverse kinematics. The projection identifies feasible motion in the end-effector domain. This projection allows for a general solution that works for tools having different degrees of freedom and will converge on a solution.

20 Claims, 6 Drawing Sheets

(56) References Cited

U.S. PATENT DOCUMENTS

| | | | |
|---|---|---|---|
| 10,617,480 B2* | 4/2020 | Brisson | B25J 9/1607 |
| 10,695,136 B2* | 6/2020 | Larkin | A61B 34/37 |
| 10,807,242 B2* | 10/2020 | Zhou | B25J 9/1689 |
| 11,399,908 B2* | 8/2022 | Diolaiti | A61B 1/00087 |
| 11,534,251 B2* | 12/2022 | Nowlin | A61B 34/30 |
| 2011/0264109 A1* | 10/2011 | Nowlin | A61B 34/35 606/130 |
| 2012/0176306 A1 | 7/2012 | Lightcap et al. | |
| 2014/0320489 A1 | 10/2014 | Chizeck et al. | |
| 2017/0020615 A1 | 1/2017 | Koenig | |
| 2017/0095295 A1 | 4/2017 | Overmyer | |
| 2019/0105117 A1 | 4/2019 | Brisson | |
| 2019/0176334 A1 | 6/2019 | Zhou et al. | |
| 2020/0060777 A1* | 2/2020 | Nowlin | A61B 34/30 |
| 2020/0352663 A1 | 11/2020 | Klingbeil et al. | |
| 2021/0016445 A1 | 1/2021 | Zhou et al. | |
| 2021/0121257 A1 | 4/2021 | Yu | |
| 2021/0346107 A1* | 11/2021 | Nowlin | A61B 90/37 |
| 2023/0011725 A1* | 1/2023 | Klingbeil | A61B 34/35 |

OTHER PUBLICATIONS

Kucuk, Serdar, and Zafer Bingul. Robot kinematics: Forward and inverse kinematics. INTECH Open Access Publisher, 2006. pp. 117-148.

Moulton, Joshua, James Pellegrin, and Matthew Stephenson. "Planar Robots and the Inverse Kinematic Problem: An Application of Groebner Bases." pp. 1-12. Retrieved Jun. 30, 2021.

The International Search Report and Written Opinion of the International Searching Authority for International Application No. PCT/IB2022/055441 Mailed Sep. 19, 2022.

\* cited by examiner

PROJECTION OPERATOR FOR INVERSE KINEMATICS OF A SURGICAL ROBOT FOR LOW DEGREE OF FREEDOM TOOLS

BACKGROUND

The present embodiments relate to robotic systems for minimally-invasive surgery (MIS). MIS may be performed with robotic systems that include one or more robotic arms for manipulating surgical tools based on commands from a remote operator. A robotic arm may, for example, support at its distal end various surgical end effectors, including scalpels, imaging devices (e.g., endoscope), clamps, and scissors. Using the robotic system, the surgeon controls the robotic arms in teleoperation during MIS.

Teleoperation converts user commands to robotic arm and surgical tool joint commands as an inverse kinematic problem. The inverse kinematic problem may need to deal with different numbers of degrees of freedom (DOF), depending on the end effector being used. For example, a clamp has six degrees of freedom in teleoperation. After braking one or more joints once positioned for operation, six active joints, and corresponding six DOF, are provided by three joints on the surgical tool (e.g., rotation, pitch, and yaw), and three joints on the robotic arm (e.g., spherical rotate, spherical pitch, and tool translate). As another example, scissors have five DOF in teleoperation. Five active joints, and corresponding DOF, includes two joints on the instrument (e.g., rotation and articulate) and three joints on the robotic arm (e.g., spherical rotate, spherical pitch, and tool translate). In yet another example, an endoscope or ultrasound scalpel has four DOF in teleoperation. Four active joints, and corresponding DOF, include one joint on the instrument (e.g., rotation) and three joints on the robotic arm (e.g., spherical rotate, spherical pitch, and tool translate).

During teleoperation, the user inputs with six DOF, which commands are translated into joints motions, such that the instrument follows the user commands with controlled accuracy. To convert user commands to joint commands, an inverse kinematic function is solved. Tools having less than six DOFs do not track with arbitrary spatial commands (position and orientation) from the user input, which has six DOF. This can lead to undesirable or un-intuitive behavior in the joint commands where the commanded motion is in a direction that is not feasible for the robot.

SUMMARY

By way of introduction, the preferred embodiments described below include methods, systems, instructions, and computer readable media for teleoperation of a surgical robotic system. The control of the surgical robotic system accounts for a limited degree of freedom of a tool in a surgical robotic system. A projection from the greater DOF of the user input commands to the lesser DOF of the tool is included within or as part of the inverse kinematics. The projection identifies feasible motion in the end-effector domain. This projection allows for a general solution that works for tools having different degrees of freedom and will converge on a solution.

In a first aspect, a method is provided for teleoperation of a surgical robotic system. A user command to move a surgical tool mounted to a robotic arm during the teleoperation is received. The user command includes rotation of the surgical tool where the surgical tool is rotatable only in less than three degrees of freedom. Motion is solved for from the user command with inverse kinematics. The solving has a projection from the user command to feasible motion based on the less than three degrees of freedom. The robotic arm or surgical tool moves based on a solution from the solving.

In a second aspect, a method is provided for accounting for a limited degree of freedom of a tool in a surgical robotic system. A difference between a change in joint position of the surgical robotic system and a change in pose of an end effector of the tool is minimized. The minimizing provides the change in the joint position given the change in pose. The difference in the minimizing is weighted with a matrix distinguishing feasible and infeasible poses of the end effector of the tool based on the limited degrees of freedom. The surgical robotic system is controlled based on the change in the joint position.

In a third aspect, a surgical robotic system is provided for medical teleoperation. A first surgical instrument connects to a robotic arm. An end effector of the first surgical instrument as connected to the robotic arm cannot rotate about at least one axis. A controller is configured to solve for motion of the first surgical instrument during the medical teleoperation on a patient and in response to user input of a move command. The solution is with inverse kinematics where the inverse kinematics includes a projection of the user input to a lower dimensional space that accounts for the lack of rotation about the at least one axis.

The present invention is defined by the following claims, and nothing in this section should be taken as a limitation on those claims. Any teaching for one type of claim (e.g., method) may be applicable to another type of claim (e.g., computer readable storage medium or system). Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A projection matrix from a greater degree of freedom of the user input commands to a lesser degree of freedom of a surgical instrument is incorporated into the inverse kinematics. In one robotic surgical system, position commands are always achievable due to the construction of a spherical arm with three DOFs. Projections modify the commanded orientations due to limited rotation by the surgical tool connected with the spherical arm. This limited rotation requires computation of the unit vector joining a reduced center of motion (RCM) and an end-effector frame (EEF). This computation becomes undefined or ill-conditioned as the tool is drawn into a cannula and the EEF to RCM distance tends to zero. In order to avoid this singularity, the EEF coordinate axes define instantaneous feasible directions of motion and map those to an inverse kinematics solver control frame, such as the spherical arm base frame. This combines the Jacobian and command projection with the inverse kinematics solution step, removing the need to explicitly handle the singularity and reducing computation.

By incorporating the projection into the inverse kinematics, a generalized framework is provided for computing projections for n-DOF tools where n is an integer of 3 or less. The need for tool specific algorithms in the teleoperation pipeline is reduced by providing the generalized framework. The need for developer designed projections based on end-effector pose is removed. A programmatic way to generate projections from tool models is developed. The RCM singularity in orientation projection computations is removed, and the computations required for projections and inverse kinematics may be reduced.

Figure 1:
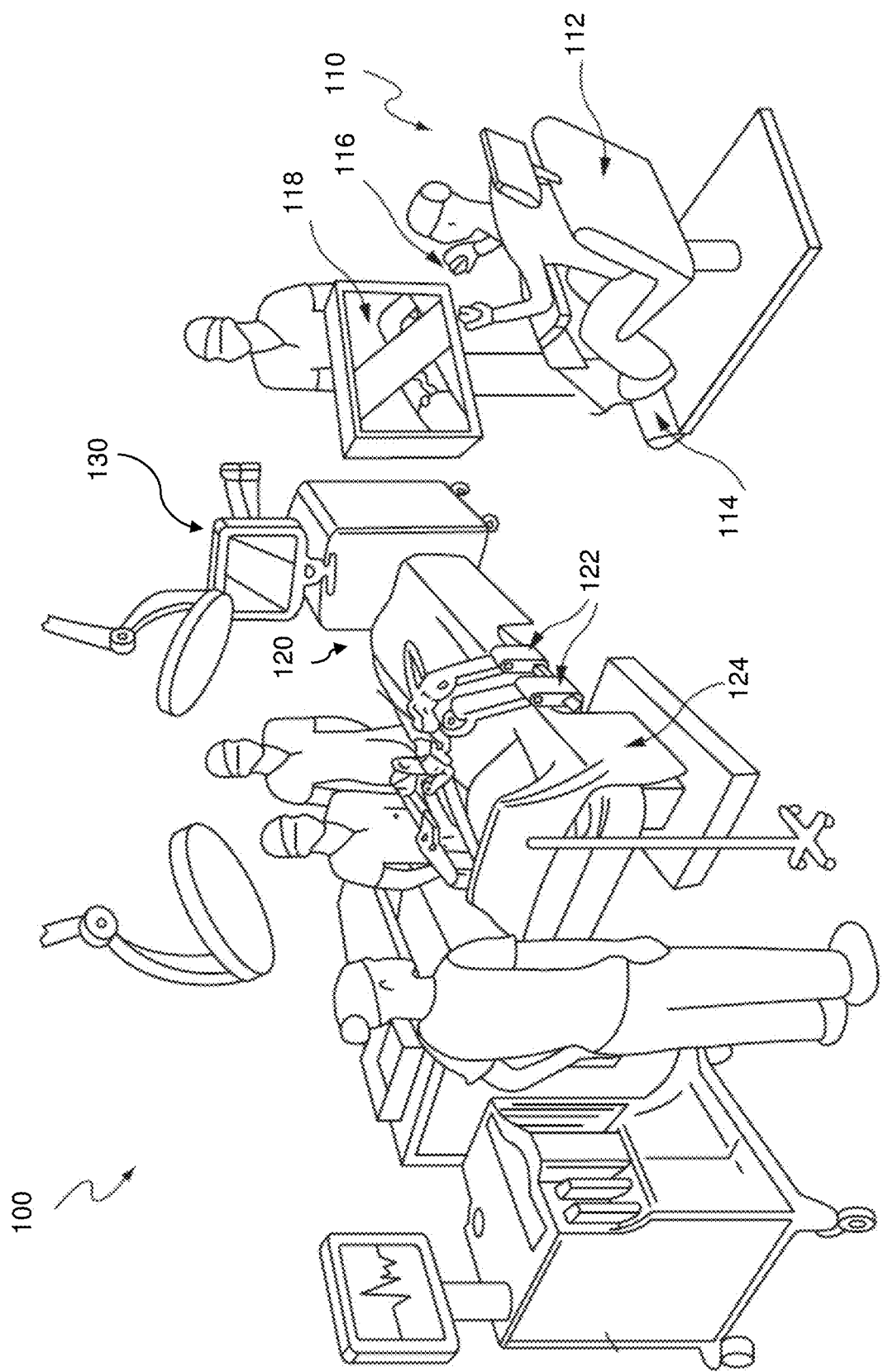
FIG. 1 is an illustration of one embodiment of an operating room environment with a surgical robotic system according to one embodiment.
Figure 2:
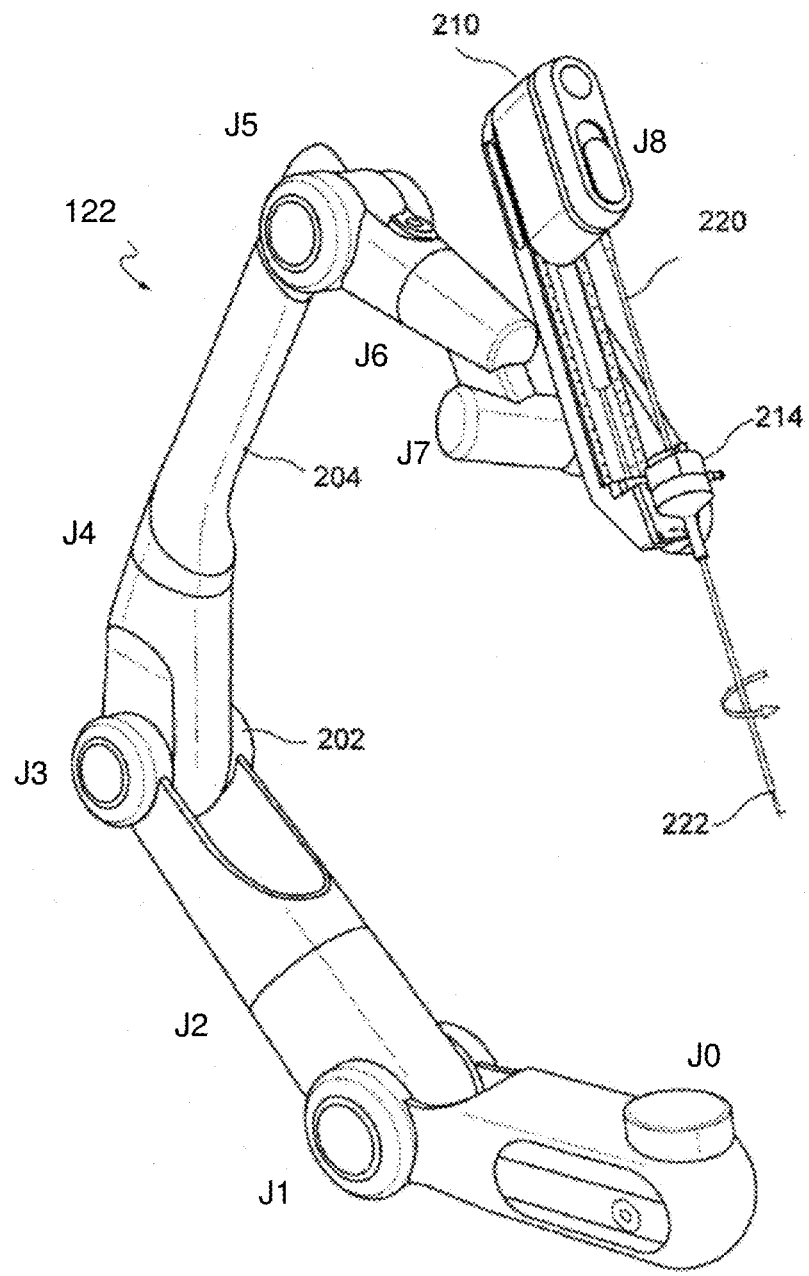
FIG. 2 illustrates an example surgical robot arm and surgical tool.

FIGS. 1 and 2 show an example surgical robotic system. The approaches for incorporating the projection into the inverse kinematics are discussed below in reference to this example system. Other surgical robotic systems and surgical robots or non-surgical robotic systems and robots may use the approaches.

Figure 3:
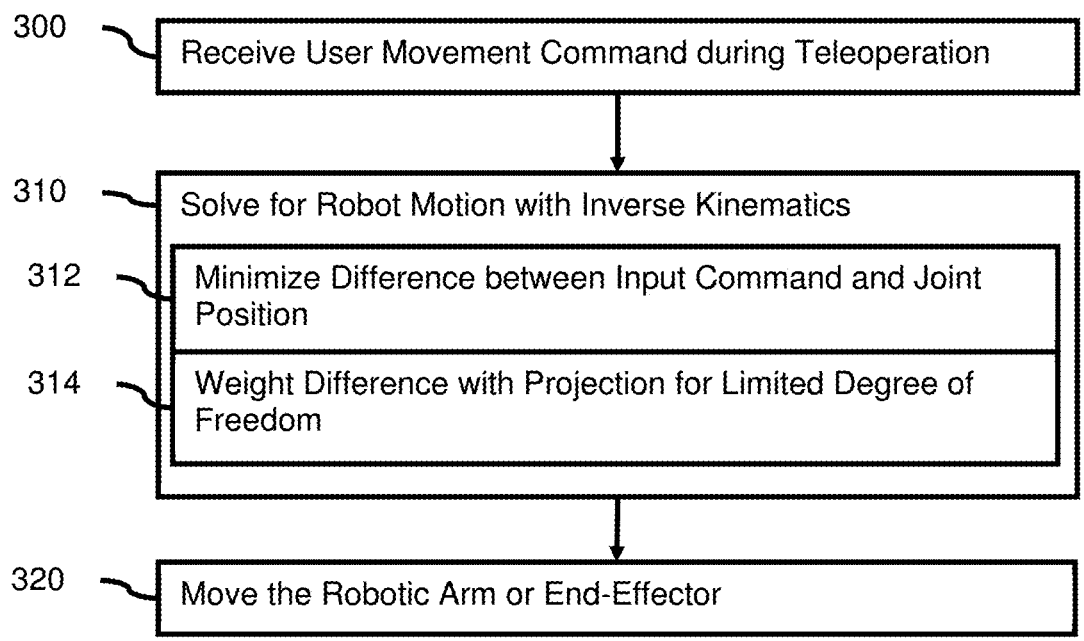
FIG. 3 is a flow chart diagram of one embodiment of a method for teleoperation of a surgical robotic system.
Figure 4:
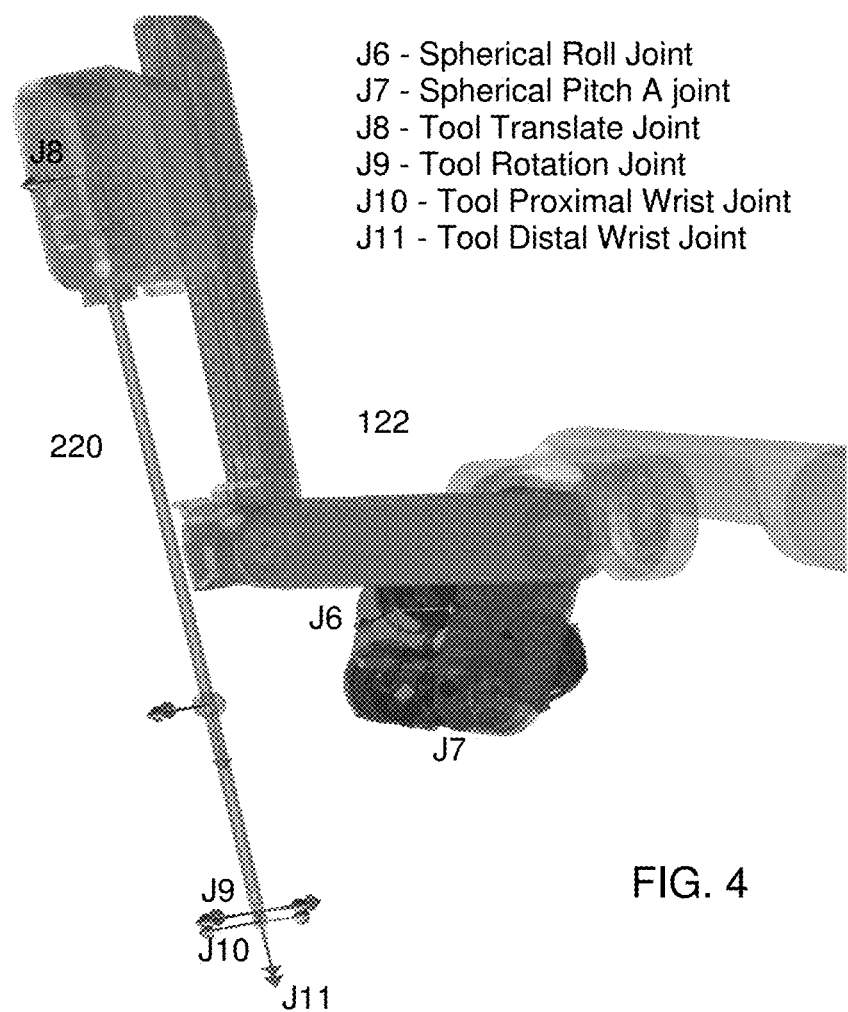
FIG. 4 shows an example robotic arm and surgical tool for six DOF.
Figure 5:
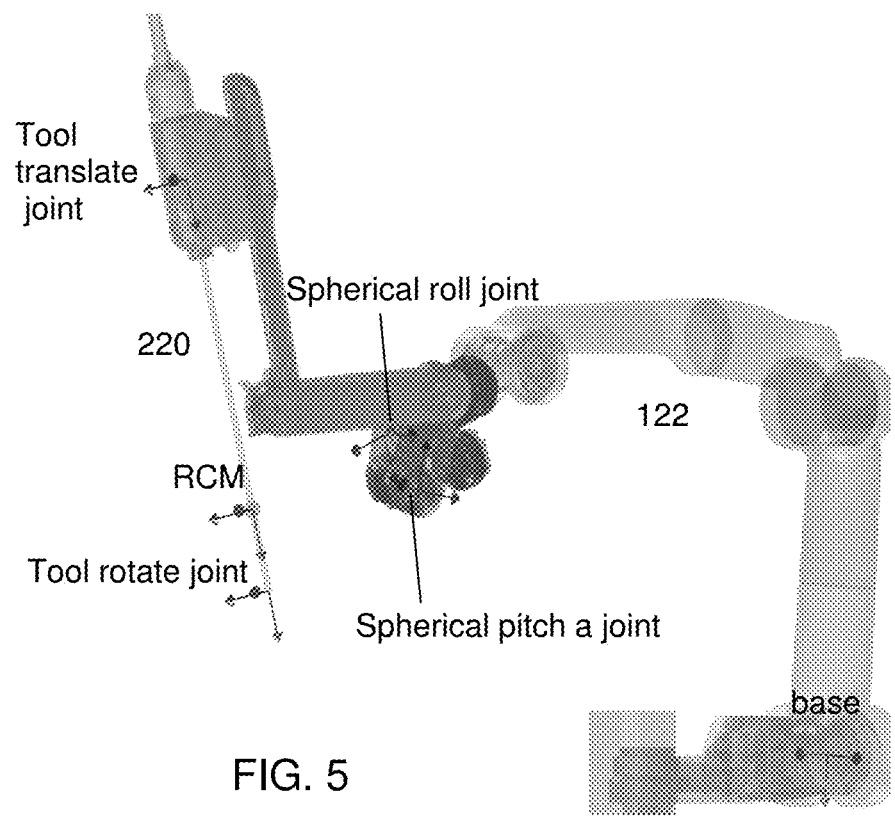
FIG. 5 shows an example robotic arm and surgical tool for four DOF.
Figure 6:
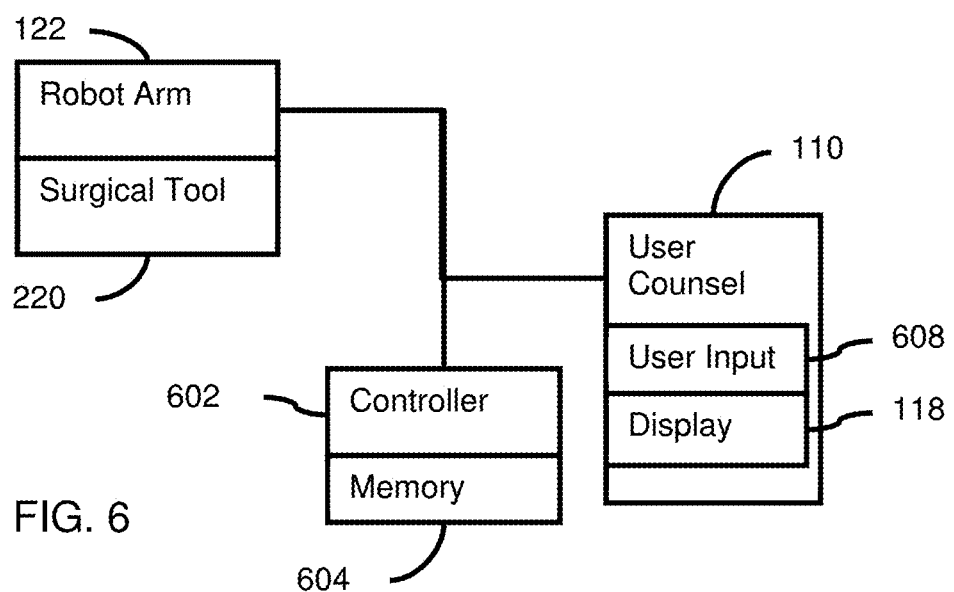
FIG. 6 is a block diagram of one embodiment of a surgical robotic system.

FIGS. 3-5 are directed to an inverse kinematic solution with an integrated projection in teleoperation. FIG. 6 is directed to a system for using the integrated projection in the inverse kinematics with a medical robotic system for teleoperation.

FIG. 1 is a diagram illustrating an example operating room environment with a surgical robotic system 100 for which commands from the user are converted into motion of the surgical robotic arms 122 with inverse kinematics. The surgical robotic system 100 includes a user console 110, a control tower 130, and a surgical robot 120 having one or more surgical robotic arms 122 mounted on a surgical platform 124 (e.g., a table or a bed etc.), where surgical tools with end effectors are attached to the distal ends of the robotic arms 122 for executing a surgical procedure. Additional, different, or fewer components may be provided, such as combining the control tower 130 with the console 110 or surgical robot 120. The robotic arms 122 are shown as table-mounted, but in other configurations, the robotic arms 122 may be mounted in a cart, a ceiling, a sidewall, or other suitable support surfaces.

Generally, a user, such as a surgeon or other operator, may be seated at the user console 110 to remotely manipulate the robotic arms 122 and/or surgical instruments (e.g., teleoperation). The user console 110 may be located in the same operation room as the robotic system 100, as shown in FIG. 1. In other environments, the user console 110 may be located in an adjacent or nearby room, or tele-operated from a remote location in a different building, city, or country. The user console 110 may include a seat 112, pedals 114, one or more handheld user interface devices (UIDs) 116, and an open display 118 configured to display, for example, a view of the surgical site inside a patient and graphic user interface. As shown in the exemplary user console 110, a surgeon sitting in the seat 112 and viewing the open display 118 may manipulate the pedals 114 and/or handheld user interface devices 116 to remotely and directly control the robotic arms 122 and/or surgical instruments mounted to the distal ends of the arms 122. The user inputs commands for the movement of the surgical arms 122 and/or end effectors. This user control determines pose (position and orientation) of the robotic arms 122. The surgeon sitting in the seat 112 may view and interact with the display 118 to input commands for movement in teleoperation of the robotic arms 122 and/or surgical instruments in the surgery.

In some variations, a user may also operate the surgical robotic system 100 in an "over the bed" (OTB) mode, in which the user is at the patient's side and simultaneously manipulating a robotically-driven tool/end effector attached thereto (e.g., with a handheld user interface device 116 held in one hand) and a manual laparoscopic tool. For example, the user's left hand may be manipulating a handheld user interface device 116 to control a robotic surgical component while the user's right hand may be manipulating a manual laparoscopic tool. Thus, in these variations, the user may perform both robotic-assisted MIS and manual laparoscopic surgery on a patient.

During an exemplary procedure or surgery, the patient is prepped and draped in a sterile fashion to achieve anesthesia. Initial access to the surgical site may be performed manually with the robotic system 100 in a stowed configuration or withdrawn configuration to facilitate access to the surgical site. Once the access is completed, initial positioning and/or preparation of the robotic system may be performed. During the procedure, a surgeon in the user console 110 may utilize the pedals 114 and/or user interface devices 116 to manipulate various end effectors and/or imaging systems to perform the surgery using teleoperation. The movements may be surgeon, patient, and/or situation specific, so may vary. Manual assistance may also be provided at the procedure table by sterile-gowned personnel, who may perform tasks including but not limited to, retracting tissues or performing manual repositioning or tool exchange involving one or more robotic arms 122. Some surgical tasks, such as retracting, suturing, or other tissue manipulation, may instead be performed by one or more robotic arms 122 (e.g., third or fourth arms). Nonsterile personnel may also be present to assist the surgeon at the user console 110. When the procedure or surgery is completed, the robotic system 100 and/or user console 110 may be configured or set in a state to facilitate one or more post-operative procedures, including but not limited to, robotic system 100 cleaning and/or sterilization, and/or healthcare record entry or printout, whether electronic or hard copy, such as via the user console 110.

In some aspects, the communication between the surgical robot 120 and the user console 110 may be through the control tower 130, which may translate user input commands from the user console 110 to robotic control commands and transmit the control commands to the surgical robot 120. The control tower 130 performs inverse kinematics. The control tower 130 may also transmit status and feedback from the robot 120 back to the user console 110. The connections between the surgical robot 120, the user console 110, and the control tower 130 may be via wired and/or wireless connections and may be proprietary and/or performed using any of a variety of data communication protocols. Any wired connections may be optionally built into the floor and/or walls or ceiling of the operating room. The surgical robotic system 100 may provide video output to one or more displays, including displays within the operating room, as well as remote displays accessible via the Internet or other networks. The video output or feed may also be encrypted to ensure privacy and all or portions of the video output may be saved to a server or electronic healthcare record system.

Prior to initiating surgery with the surgical robotic system, the surgical team can perform preoperative setup. During the preoperative setup, the main components of the surgical robotic system (e.g., table 124 and robotic arms 122, control tower 130, and user console 110) are positioned in the operating room, connected, and powered on. The table 124 and robotic arms 122 may be in a fully-stowed configuration with the arms 122 under the table 124 for storage and/or transportation purposes. The surgical team can extend the arms 122 from their stowed position for sterile draping. After draping, the arms 122 can be partially retracted until needed for use. A number of conventional laparoscopic steps may need to be performed including trocar placement and insufflation. For example, each sleeve can be inserted with the aid of an obturator, into a small incision and through the body wall. The sleeve and obturator allow optical entry for visualization of tissue layers during insertion to minimize risk of injury during placement. The endoscope is typically placed first to provide hand-held camera visualization for placement of other trocars. After insufflation, if required, manual instruments can be inserted through the sleeve to perform any laparoscopic steps by hand.

Next, the surgical team may position the robotic arms 122 over the patient and attach each arm 122 to a corresponding sleeve. The surgical robotic system 100 has the capability to uniquely identify each tool (endoscope and surgical instruments) upon attachment and display the tool type and arm location on the open or immersive display 118 at the user console 110 and the touchscreen display on the control tower 130. The corresponding tool functions are enabled and can be activated using the master UIDs 116 and foot pedals 114. The patient-side assistant can attach and detach the tools, as required, throughout the procedure. The surgeon seated at the user console 110 can begin to perform surgery as teleoperation using the tools controlled by two master UIDs 116 and foot pedals 114. The system translates the surgeon's hand, wrist, and finger movements through the master UIDs 116 into precise real-time movements of the surgical tools. Therefore in direct teleoperation, the system constantly monitors every surgical maneuver of the surgeon and pauses instrument movement if the system is unable to precisely mirror the surgeon's hand motions. The UIDs 116 may move in six DOF, such as allowing translation in three dimensions and rotation about the three dimensions. The foot pedals 114 may be used to activate various system modes, such as endoscope control and various instrument functions including monopolar and bipolar cautery, without involving surgeon's hands removed from the master UIDs 116.

FIG. 2 is a schematic diagram illustrating one exemplary design of a robotic arm, a tool drive, and a cannula loaded with a robotic surgical tool, in accordance with aspects of the subject technology. As shown in FIG. 2, the example surgical robotic arm 122 may include a plurality of links (e.g., a link 202) and a plurality of actuated joint modules (e.g., a joint 204, see also joints J1-8) for actuating the plurality of links relative to one another. The joint modules may include various types, such as a pitch joint or a roll joint, which may substantially constrain the movement of the adjacent links around certain axes relative to others. Also shown in the exemplary design of FIG. 2 is a tool drive 210 attached to the distal end of the robotic arm 122. The tool drive 210 may include a cannula 214 coupled to its end to receive and guide a surgical instrument or end effector 220 (e.g., endoscopes, staplers, scalpel, scissors, clamp, retractor, etc.). The surgical instrument (or "tool") 220 may include an end effector 222 at the distal end of the tool. The plurality of the joint modules of the robotic arm 122 can be actuated to position and orient the tool drive 210, which actuates the end effector 222 for robotic surgeries. The end effector 222 is at a tool shaft end. In other embodiments, the tool shaft end is a tip of a needle or other object.

In the example of FIG. 2, the joint J0 is a table pivot joint and resides under the surgical table top. Joint J0 is nominally held in place during surgery. Joints J1 to J5 form a setup or Cartesian arm and are nominally held in place during surgery, so do not contribute to motion during surgical teleoperation. Joints J6 and J7 form a spherical arm that may actively move during surgery or teleoperation. Joint J8 translates the tool 220, such as the end effector 222, as part of a tool driver. Joint J8 may actively move during surgery. Joints J6-8 actively position a tool shaft end (i.e., end effector 222) during surgery while maintaining an entry point into the patient at a fixed or stable location (i.e., remote center of motion) to avoid stress on the skin of the patient. During set-up, any of the joints J0-J8 may move. During surgery, the joints J6-8 may move subject to hardware or safety limitations on position, velocity, acceleration, and/or torque. The surgical tool 220 may include none, one, or more (e.g., three) joints, such as a joint for tool rotation plus any number of additional joints (e.g., wrists, rotation about a longitudinal axis, or other type of motion). Any number of degrees of freedom may be provided, such as the three degrees from the joints J6-8 and none, one, or more degrees from the surgical tool 220.

FIG. 3 is a flow chart diagram of one embodiment of a method for teleoperation of a surgical robotic system. The method accounts for any limited DOF of a tool or surgical instrument. Inverse kinematics are used to convert user commands to a solution for movement of a robotic arm and surgical tool. To address the limited DOF of the tool, a projection is integrated or included in the inverse kinematics. The minimization or other optimization for the inverse kinematics is weighted by feasible and infeasible motion of the tool.

The method of FIG. 3 is implemented by a control processor, such as the control tower 130, computer, workstation, sever, or another processor performing act 310. Any computer of the surgical robotic system 100 may be used. A user interface provides the movement commands from the user received in act 300. The robotic arm 122 and/or surgical tool 220 are moved using the instructions or control from the control processor in act 320. Other devices may perform and/or be used in any of the acts.

The acts are performed in the order shown or other orders. The various acts 312 and 314 that are part of the solving of act 310 may be performed in any order and/or simultaneously (e.g., as part of the same solution using inverse kinematics translating user commands to robotic arm and surgical tool movement).

Additional, different, or fewer acts may be used. For example, act 320 is not provided. As another example, the movement commands are from a programmed or processor determined sequence (e.g., operation template), so act 300 is not provided. In another example, acts for initially positioning the surgical tool 220 in the patient, planning surgery, and/or removing the surgical tool 220 from the patient may be provided.

In act 300, the control processor receives a user command to move the surgical tool 220 through movement of the robotic arm 122 or surgical tool 220 of the robotic arm 122 during the teleoperation. The user input is received from the user console 110, such as the pedals 114 or user interface devices 116, via wireless or wired interface by the control processor. In other embodiments, the user commands are received by loading from memory or transmission over a computer network.

In preparation for teleoperation, the user sits down at the surgeon console 110. After positioning of the robot arm 122 for teleoperation, one or more joints are locked in place with a fixed remote center of motion (RCM) at the patient skin or incision entry point. For example, joints J0-J5 (see FIG. 2) are locked. The locking is by a brake and/or avoiding energizing the motors for the joints. These joints remain locked during teleoperation.

During teleoperation, the user enters commands to move the surgical tool 220. The commands are for motion of the surgical tool 220. Different commands may be provided for different movements. The commands may be for movement of the end effector 222. A change in pose of the end effector is entered. These commands may not be for movement of particular joints. The control processor is to convert the movement commands of the end effector or user input to controls of particular joints of the robotic arm 122 and/or surgical tool 220.

In one embodiment, user motion is tracked using a sensor. For example, the user holds a device, such as a pen or a UID 116. A magnetic position sensor and/or inertial measurement unit may be used to determine position and/or change in position of the pen or UID 116. As another example, the user holds a marker with a structure allowing for visual tracking, such as optical patterns or structures on one or more parts of the marker. A stereo camera and/or depth camera tracks the motion of the marker. Other user input devices may be used.

The user commands are in six DOF. Translation along and rotation about all of three orthogonal axes is provided. The user commands may be for control of a surgical instrument 220 or end effector with fewer than six DOF, such as four or five DOF (e.g., translation along three axes but rotation along one or two axes).

The user commands may be for movement in any number of DOF. FIG. 4 shows part of the robotic arm 122 and the surgical tool 220 providing six DOF. The six DOF correspond to movement of six active joints during teleoperation. The active joints include three joints on the surgical tool 220—rotation at joint J9, pitch at wrist joint J10, and yaw at wrist joint J11. The active joints include three joints on the robotic arm 122—spherical rotation joint J6, spherical pitch joint J7, and tool translation joint J8. Other joints providing the six degrees of freedom may be used.

The user commands may be for movement for fewer than six degrees of freedom. Five, four, or fewer active joints may be provided. FIG. 5 shows the robotic arm 122 and the surgical tool 220 providing four DOF, such as where the surgical tool 220 is an endoscope or ultrasound scalpel. The active joints include three joints on the robotic arm 122—spherical rotation joint J6, spherical pitch joint J7, and tool translation joint J8. The active joints include one joint on the surgical tool 220—rotation at joint J9. In an example of five DOF, the active joints include three joints on the robotic arm 122—spherical rotation joint J6, spherical pitch joint J7, and tool translation joint J8—and two actives joints on the surgical tool—rotation at joint J9 and articulation as another joint). Other active joint arrangements may be used, such as providing two or fewer DOF on the robotic arm during teleoperation.

The DOF of the user commands is the same or greater than the DOF of movement of the end effector. For example, the tool 220 has a limited degree of freedom, such as four or five DOF in combination of the tool 220 with the robotic arm 122 during teleoperation. The user commands and corresponding UIDs 116 have six DOF. This may result in receiving user commands with rotation and/or translation of the tool about or along an axis where the tool is not rotatable about or translatable along that axis. In the example of FIG. 5, the tool may be rotatable about a single axis, yet the user commands may include rotation of the end effector about all or any of three axes.

In act 310, the controller or another processor solves for joint motion from the user command with inverse kinematics. The control processor translates the movement commands from the user to movement of the joints. The control processor solves for motion by the robotic arm 122 and/or the surgical tool 220 of the robotic arm 122 with an iterative solution. An iterative inverse kinematic solution is found.

Any control process may be used. The control process may be input of the user commands, iterative solution using inverse kinematics with a given termination check for the iterations, and output of a final result of joint commands. The inverse kinematics may incorporate limits on position, velocity, torque, and/or acceleration on the motion of the end effector and/or joints. The inverse kinematics is an optimization function, such as a minimization. For example, a difference between a change in joint position of the surgical robotic system and a change in pose of an end effector of the tool (i.e., change translated from user command) is minimized in act 312. The minimization provides for the change in the joint position given the change in pose. Other optimizations may be used.

In one embodiment, the inverse kinematics is performed as a least square minimization. Other minimizations may be used. The minimization is solved from in a control frame different than the end effector coordinate system. For example, the control frame is a frame of reference for the robotic arm 122, such as a coordinate system based on the joint J0 or a base of the robotic arm 122.

In the example of the robotic arm 122 of FIG. 2, the inverse kinematics may solve for joint motion where the surgical tool 220 has less than three joints or three DOF. Including the three DOFs from the robotic arm 122, the inverse kinematics satisfies six constraints or objectives with joints having fewer DOF (e.g., <6). This results in an over-constrained problem, which may not have a solution. In such a case, the least square inverse attempts to minimize the difference between the command ($x_{command}$) and feasible spatial position and rotation, represented as:

$$(x_{feasible} = J \cdot q_{feasible}), \text{ i.e. arg min} |x_{command} - x_{feasible}(q)|\\ |=q^*$$

Any change in $x_{command}$, produces a change in $q^*$, the matrix of joint commands. This is true even when the instantaneous twist from the current position $x_{current}$ to $x_{command}$, $\tau = x_{command} - x_{current}$, requires motion in a direction that is not achievable due to restrictions from the tool design (i.e., limited DOF of the tool). Since this is unintended and unintuitive behavior, $x_{command}$ is projected to ensure that the command lies in the column space of the Jacobian.

The projection is from the user command or end effector to feasible motions given the limited DOF of the surgical tool 220. The solution is in the control frame, so the projection is from the user command or end effector space to the control frame for the robotic arm 122 and surgical tool 220. The projection is included as part of or within the inverse kinematics. The projection operator is part of the function being optimized. For example, the projection is a weight in the inverse kinematics. In act 314, the difference in minimizing is weighted with a matrix distinguishing feasible and infeasible poses of the end effector of the tool 220 based on the limited DOFs of the tool 220.

In one embodiment, the computation of the projection operator uses determination of instantaneous axes about which translations and rotations are feasible under hardware constraints. These are then compiled into the columns of rotation (SR) and translation (ST) selection matrices. Using the robotic arm 122 of FIG. 2 with joints J0-J5 locked during teleoperation, the spherical joints (e.g., spherical roll joint J6, spherical pitch joint J7 and tool translate joint J8) form a spherical coordinate system centered at the RCM (e.g., joint J6 corresponding to the polar angle θ, joint J7 corresponding to the azimuthal angle φ, and joint J8 corresponding to the radial distance r). All task space positions are achievable. Any set of perpendicular axes will satisfy the requirements of ST. These axes are selected to be basis vectors of the end effector.

For SR, depending on the DOFs, rotations about one or more axes may be tracked accurately. For four DOF tools 220 (e.g., FIG. 5), the rotation is about the tool joint axis. For example, a harmonic scalpel or endoscope has one axis (e.g., the X-axis) of rotation. In the end effector space or coordinate system, the matrix is represented as:

$$S_R = \begin{bmatrix} 1 & 0 & 0 \\ 0 & 0 & 0 \\ 0 & 0 & 0 \end{bmatrix}$$

Due to the absence of tool wrists, only rotations about the end effector x-axis are feasible at any time. The weight 1 represents feasible rotation, while the weights 0 represent infeasible or impossible rotations. This selection matrix indicates the available rotations for the selected tool 220. Non-binary weightings may be used. Other matrix positions, such as for feasible rotation about another axis, may have the non-zero weighting.

For a surgical tool 220 with five DOF, two axes may be selected for rotation. In the end effector space or coordinate system, the selection matrix is represented as:

$$S_R = \begin{bmatrix} 1 & 0 & 0 \\ 0 & 1 & 0 \\ 0 & 0 & 0 \end{bmatrix}$$

The two "1" values provide for two axes of rotation for the tool. Other locations in the matrix may have the feasible rotation weights, such as for other types of tools.

For a surgical tool having six or higher DOF, all rotations are feasible. Any arbitrary perpendicular basis can be selected leading to:

$$S_R = \begin{bmatrix} 1 & 0 & 0 \\ 0 & 1 & 0 \\ 0 & 0 & 1 \end{bmatrix}$$

The three "1" values provide for rotation about all three spatial axes being feasible. During teleoperation, instantaneous rotations about any arbitrary axis is feasible due to the tool 220 having three DOF and the robotic arm having three DOF (i.e., 6 DOF). For example, the surgical instrument has two wrists and a tool base rotation as joints.

These selection matrices are represented in the end effector space to correspond to the axes operable for the end effector. The selection matrix for a given tool is mapped to the frame in which the inverse kinematics solver operates, such as the control frame, CF. The selection matrix for feasible rotation and/or translation is multiplied with the mapping or conversion. An example representation is given by:

$$P = \begin{bmatrix} CF\ R_{EEF} & 0 \\ 0 & CF\ R_{EEF} \end{bmatrix} \begin{bmatrix} S_T & 0 \\ 0 & S_R \end{bmatrix} \begin{bmatrix} CF\ R_{EEF}^T & 0 \\ 0 & CF\ R_{EEF}^T \end{bmatrix}$$

where P is the projection operator, EEF represents the end effector space, and R is the rotation transform. For example, P is a 6×6 projection operator, $S_T$ is the translation selection matrix of unit vectors of feasible translation motions in the end effector space EEF, $S_R$ is the rotation selection matrix of unit length feasible axes of rotation, and CF $R_{EEF}$ is the rotation matrix from EEF to CF.

The rotation selection matrix prevents changes in position for infeasible poses. By projecting to the control frame, the solution for joint positions avoids infeasible rotation due to the weighting. The projection operator is used as a weight in the function being optimized in inverse kinematics. For example, the difference being minimized is weighted with the projection operator projecting to the limited degree of freedom. The limited degree of freedom of the tool is a limitation in rotation of the tool 220. The projection operator includes the rotation selection matrix, which indicates the feasible and infeasible rotations of the tool 220. The rotation selection matrix is multiplied with a Jacobian of the inverse kinematics to weight. In the least square example, the inverse kinematics is reformulated as:

min ½$(J\Delta q-\Delta x)^T P(J\Delta q-\Delta x)$ $\Rightarrow J^T PJ\Delta q = J^T P\Delta x$ where the projection operator weights the Jacobian of the difference. A weighted minimization framework is used. This has the effect of weighing the feasible motions with weight 1 and infeasible motions with weight 0, removing undesirable coupling effects. The solution to this unconstrained minimization is $\Delta q^*$ where $J^T PJ\Delta q^* = J^T P\Delta x$. This problem can be further augmented to handle joint or other limits and solved as a constrained optimization. By optimizing, joint commands to fulfill the user movement command are output.

The block diagonal structure of the selection matrix and the mechanical construction of the spherical arm may be exploited to speed up computation of the selection operator as follows:

$$P = \begin{bmatrix} CF\ R_{EEF}S_T\ CF\ R_{EEF}^T & 0 \\ 0 & CF\ R_{EEF}S_R\ CF\ R_{EEF}^T \end{bmatrix}$$

$$\Rightarrow P = \begin{bmatrix} 1 & 0 \\ 0 & CF\ R_{EEF}S_R\ CF\ R_{EEF}^T \end{bmatrix}$$

Similar speeds ups may be performed for the matrix products $J^T PJ$ and $J^T P\Delta x$ depending on the solver being used.

The projection operator may also be used to formulate anisotropic taskspace constraints for virtual fixturing, repositioning, or another purpose. A virtual boundary is incorporated, such as to give feedback to the user. For example for a virtual fixture about point $x_{fixture}$, the inverse kinematics uses the boundary, such as represented by:

$$J^T PJ\Delta q = J^T Pk(x_{fixture} - x_{estimate})$$

Additionally, the selection matrices ST and SR may be represented in an arbitrary frame F with the computation of the projection operator modified as represented more generally as:

$$P = \begin{bmatrix} CF\ R_F & 0 \\ 0 & CF\ R_F \end{bmatrix} \begin{bmatrix} S_T^F & 0 \\ 0 & S_R^F \end{bmatrix} \begin{bmatrix} CF\ R_F^T & 0 \\ 0 & CF\ R_F^T \end{bmatrix}$$

In act 320, the control processor causes movement of the robotic arm 122 and/or the surgical tool 220. The output movement commands for the active joints during teleoperation cause the joints to change position at the velocity and/or acceleration. The results from the inverse kinematics control the movement of the joints (e.g., joints J6-9 of FIG. 4). The joint motion avoids rotation of the surgical tool 220 in ways that are not feasible. The solution from the inverse kinematics is used to move the surgical tool 220 by operation of joints of the surgical tool 220 and/or joints of the robotic arm 122 holding the surgical tool 220. The solved for changes in joint position control the surgical robotic system.

FIG. 6 shows a block diagram of one embodiment of a surgical robotic system for medical teleoperation. The inverse kinematics for operating the surgical robotic system include a projection of the user input to a lower dimensional space that accounts for the lack of rotation about at least one axis of the surgical tool 220. The system performs the method of FIG. 3 or another method.

The surgical robot system includes one or more robot arms 122 with corresponding surgical instruments 220 or other types of instruments connected with the robot arms 122, a controller 602, and a memory 604. The user console 110 is represented or included as part of the surgical robot system but may be positioned remotely from or locally to the robot arm 122. Additional, different, or fewer components may be provided. For example, the robot arm 122, surgical instrument 220, and/or user console 110 are not provided.

The robotic arms 122 each include one or more links and joints. The joints may be pitch or roll joints. A tool drive and cannula for receiving and guiding a surgical tool may be provided on each of the robotic arms 122. Different combinations of links and joints may define or form different parts of the robotic arms 122, such as different parts having different degrees or types of movement (e.g., translation and/or rotation). Any now known or later develop robotic arm 122 with motors, sensors, links, joints, controllers, surgical instruments, and/or other structure may be used.

One or more robotic arms are provided. For example, three or four robotic arms 122 are provided. The robotic arms 122 mount to a table, such as a base of an operating table. Alternatively, cart, floor, ceiling, or other mounts may be used. The robotic arms 122 include a cable or wireless transceiver for communication with the processor 206 or an intermediary (e.g., control tower 130).

The robotic surgical instruments 220 are one or more graspers, retractors, scalpels, endoscopes, staplers, scissors, or other surgical device for manipulating tissue of the patient. The tissue manipulation may be direct, such as cutting or grasping. The tissue manipulation may be indirect, such as an endoscope pressing or contacting tissue as guided to image or view an interior portion of the patient. Different or the same type of instruments 220 may be mounted to different ones of the robot arms 122. For example, two robot arms 122 may have graspers, a third robot arm 122 may have a scalpel, and a fourth robot arm 122 may have an endoscope.

The robotic surgical instruments 220 connect to the distal ends of the robot arms 122 but may connect at other locations. The connection provides a drive so that the tool may be operated, such as closing a grasper or scissors.

One or more of the robotic surgical instruments 220 has limited motion. The surgical instrument 220 in combination with the robot arm 122 may have fewer than six DOF, such as having four or five DOF. For example, the robot arm 122 provides three joints while the surgical instrument 220 is limited to rotation about one axis or two axes. An endoscope as the surgical tool 220 may provide for just rotation about the long axis of the instrument 220 without rotation about two other orthogonal axes. While the robot arm 122 may allow for full 6 DOF, the surgical instrument is more limited. The robot arm 122 may have some movement locked during teleoperation. As a result, the surgical instrument 220 or the surgical instrument in combination with the robot arm 122 may not be able to rotate and/or translate about one or more axes.

The user console 110 is a graphics user interface for interaction of the surgeon with the surgical robot system, such as with a processor for controlling the robotic arms 122. The user interface includes a user input 608 and a display 118. The user input 608 and/or the display 118 are provided at the user console 110 and/or control tower 130 but may be at other locations.

The user input 608 is a button, a keyboard, a rocker, a joy stick, a trackball, a voice recognition circuit, a mouse, a touch pad, a touch screen, sliders, switches, UID 116, foot pedal 114, combinations thereof, or any other input device for inputting to the surgical robot. The display 118 is a monitor, liquid crystal display (LCD), projector, plasma display, CRT, printer, or other now known or later developed device for outputting visual information. In an alternative embodiment, the display 118 is a head mounted display. The user input 608 may be a sensor or sensors for detecting eye movement and/or blinking. In yet other embodiments, the user input 608 is a microphone for voice-based input. A speaker for output of audio information may be provided instead of or in addition to the display 118.

The controller 602 is a controller that drives and/or models the robotic arms 122 and/or surgical instruments 220. The controller 602 is a general processor, central processing unit, control processor, graphics processor, graphics processing unit, digital signal processor, application specific integrated circuit, field programmable gate array, digital circuit, analog circuit, artificial intelligence processor, combinations thereof, or other now known or later developed device for translating user commands to joint commands for the robot arm 122 and/or surgical instrument 220. The controller 602 is a single device or multiple devices operating in serial, parallel, or separately. The controller 602 may be a main processor of a computer, such as a laptop, server, workstation, or desktop computer, or may be a processor for handling some tasks in a larger system. Based on hardware, software, firmware, or combinations thereof, the controller 602 is configured to implement instructions or perform acts.

The controller 602 is configured to solve for motion of the surgical instrument 220 during the medical teleoperation on a patient. The motion of the surgical instrument 220 is provided as joint commands to move the joints of the robot arm 122 and/or surgical instrument 220. These joint commands or motion are solved for in response to user input of a move command. The user inputs a command to move the end effector of the surgical instrument 220. The controller 602 is configured to solve for the motion of the surgical instrument 220 through operation of the joints.

The controller 602 is configured to solve for the motion with inverse kinematics. For example, a least square minimization of a difference between the motion of the surgical instrument 220 and the user input is used. Other optimizations relating the joint commands to the end effector movement commands input by the user may be used.

The inverse kinematics includes a projection of the user input to a lower dimensional space that accounts for the lack of rotation and/or translation about at least one axis. The input user commands may be associated with a greater DOF than provided by the robot arm 122 and/or surgical instrument 220. The projection reduces the DOF as part of the inverse kinematics. In one embodiment, the projection is a selection matrix for rotation of the end effector. The selection matrix distinguishes permitted and not permitted rotations of the end effector in an end effector space. The inverse kinematics is solved in a robot arm frame of reference, such as a control frame based on a base or joint J0 of the robot arm 122. The projection includes mapping from the end effector-defined feasible and infeasible motions to the control frame. For example, the projection defines instantaneous feasible motion of the end effector mapped to the control frame. The inverse kinematics is a combination of a Jacobian and the projection.

Different surgical instruments 220 have different numbers of DOF. Rather than using separate control algorithms, the matrix defining feasible and infeasible motion is altered to define for the particular instrument 220 in a single control algorithm. The same optimization, inverse kinematics with the incorporated projection from the matrix, is used regardless of the instrument 220. The solution approach is operable for different surgical instruments where the matrix or projection changes for the different limitations on the movement. Different translation and/or rotation matrices are used for different combinations of DOF. Rather than using specialized projections implemented for each tool, the matrices are changed. The specialized implementations typically suffer from higher computational cost, lack of generality and singularities at the RCM. By incorporating the generalized projection into inverse kinematics rather than projecting to limit the user command or limit the output solution, a generalized solution with lower computational cost that avoids singularities may be provided.

The controller 602 is configured to control the robot arm 122 and surgical tool 220. Based on the solution from the inverse kinematics, one or more joints are moved in response to user commands. The iterative inverse kinematic solution controls the joints.

The memory 604 or another memory is a non-transitory computer readable storage medium storing data representing instructions executable by the programmed controller 602. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for teleoperation of a surgical robotic system, the method comprising:
receiving a user command to move a surgical tool mounted to a robotic arm, the user command including rotation of the surgical tool where the surgical tool is rotatable only in less than three degrees of freedom;
solving for motion from the user command with inverse kinematics, the solving having a projection from the user command to feasible motion based on the less than three degrees of freedom, wherein solving comprises solving with a rotation selection matrix in the projection, the rotation selection matrix being in an end effector coordinate system of the surgical tool and indicating feasible and not feasible rotations; and
moving the robotic arm or surgical tool based on a solution from the solving.

2. The method of claim 1 wherein receiving comprises receiving the user command where the surgical tool is rotatable in only one degree of freedom.

3. The method of claim 1 wherein solving comprises solving with the projection restricting to feasible rotations.

4. The method of claim 1 wherein solving comprises solving with minimization that includes the projection, the solving being with a least square for the minimization.

5. The method of claim 1 wherein receiving comprises receiving the user command with rotation in three degrees of freedom where the surgical tool is only rotatable in one or two degrees of freedom.

6. The method of claim 1 wherein the surgical tool has a single degree of freedom for the rotation, and wherein solving comprises solving with the rotation selection matrix in the projection, the rotation selection matrix comprising a 3×3 matrix with zeros for all entries but one, the one entry corresponding to the single degree of freedom of the rotation of the surgical tool.

7. The method of claim 1 wherein the surgical tool has only two degrees of freedom for the rotation, and wherein solving comprises solving with the rotation selection matrix in the projection, the rotation selection matrix comprising a 3×3 matrix with zeros for all entries but two, the two entries corresponding to the two degrees of freedom of the rotation of the surgical tool.

8. The method of claim 1 wherein solving comprises solving in a control frame different than the end effector coordinate system by multiplication of the rotation selection matrix with a Jacobian of the inverse kinematics.

9. A method for teleoperation of a surgical robotic system, the method comprising:
- receiving a user command to move a surgical tool mounted to a robotic arm, the user command including rotation of the surgical tool where the surgical tool is rotatable only in less than three degrees of freedom;
- solving for motion from the user command with inverse kinematics, the solving having a projection from the user command to feasible motion based on the less than three degrees of freedom, wherein solving comprises weighting the feasible motion with a weight of 1 and infeasible motion with a weight of 0; and
- moving the robotic arm or surgical tool based on a solution from the solving.

10. A method for accounting for a limited degree of freedom of a tool in a surgical robotic system, the method comprising:
- minimizing a difference between a change in joint position of the surgical robotic system and a change in pose of an end effector of the tool, the minimizing providing the change in the joint position given the change in pose;
- weighting the difference in the minimizing with a matrix distinguishing feasible and infeasible poses of the end effector of the tool based on the limited degrees of freedom; and
- controlling the surgical robotic system based on the change in the joint position.

11. The method of claim 10 wherein minimizing comprises performing inverse kinematics as a least square minimization.

12. The method of claim 10 further comprising receiving a user input command from a user interface, the change in pose of the end effector being provided as the user input command, where the user input command is free of the limited degree of freedom of the tool and the weighting with the matrix prevents the changes in position for infeasible poses.

13. The method of claim 10 wherein weighting comprises weighting the difference with a projection operator projecting to the limited degree of freedom, the matrix being part of the projection operator.

14. The method of claim 10 wherein the limited degree of freedom is a limitation in rotation of the tool, and wherein weighting comprises weighting with the matrix, the matrix having binary weights for rotation with 1 for feasible rotation and 0 for infeasible rotation.

15. A surgical robotic system for medical teleoperation, the surgical robotic system comprising:
- a robotic arm;
- a first surgical instrument connected to the robotic arm, where an end effector of the first surgical instrument as connected to the robotic arm cannot rotate about at least one axis; and
- a controller configured to solve for motion of the first surgical instrument during the medical teleoperation on a patient and in response to user input of a move command, the solution being with inverse kinematics, the inverse kinematics including a projection of the user input from a higher dimensional space to a lower dimensional space that accounts for the lack of rotation about the at least one axis, wherein the projection comprises a selection matrix for rotation of the end effector, the selection matrix distinguishing permitted and not permitted rotations of the end effector in an end effector space.

16. The surgical robotic system of claim 15 wherein the inverse kinematics is a least square minimization of a difference between the motion of the first surgical instrument and a change from the user input, the change of the user input being for motion of the end effector, and wherein the projection comprises a projection of the user input with a greater degree of freedom to the motion of the first surgical instrument with a lesser degree of freedom.

17. The surgical robotic system of claim 15 wherein the solution is operable for different surgical instruments, including the first surgical instrument, where the different surgical instruments have different limitations on movement, the projection being different for the different limitations on the movement.

18. The surgical robotic system of claim 15 wherein the projection defines instantaneous feasible motion of the end effector mapped to a control frame, the inverse kinematics being a combination of a Jacobian and the projection.

19. The method of claim 9 wherein receiving comprises receiving the user command with rotation in three degrees of freedom where the surgical tool is only rotatable in one or two degrees of freedom.

20. The method of claim 9 wherein solving comprises solving with the projection restricting to feasible rotations.

* * * * *